United States Patent [19]

Kothari

[11] 3,935,247

[45] Jan. 27, 1976

[54] OXIDATION OF ALKYLATED PHENOLS TO P-BENZOQUINONES

[75] Inventor: Vipin M. Kothari, Akron, Ohio

[73] Assignee: The Goodyear Tire & Rubber Company, Akron, Ohio

[22] Filed: Sept. 28, 1973

[21] Appl. No.: 401,726

[52] U.S. Cl............................ 260/396 R; 260/396 N
[51] Int. Cl.².......................................... C07C 49/64
[58] Field of Search ................................ 260/396 R

[56] References Cited
UNITED STATES PATENTS

| | | | |
|---|---|---|---|
| 3,219,625 | 11/1965 | Blanchard et al.............. | 260/396 R |
| 3,219,626 | 11/1965 | Blanchard et al................. | 260/396 |
| 3,455,880 | 7/1969 | Kobayashi et al............... | 260/396 R |
| 3,549,670 | 12/1970 | Spousta........................ | 260/396 R |
| 3,658,852 | 4/1972 | Schuster et al. ................ | 260/396 R |

OTHER PUBLICATIONS

Jada et al., Bull. Chem. Soc. Japan, Vol. 45, No. 8, pp. 2558–2559, 1972.

*Primary Examiner*—Vivian Garner
*Attorney, Agent, or Firm*—F. W. Brunner; J. Y. Clowney

[57] ABSTRACT

This invention concerns a process for oxidizing alkyl substituted phenols to p-benzoquinones with oxygen in the presence of cupric and cobaltous phthalocyanine catalysts.

5 Claims, No Drawings

OXIDATION OF ALKYLATED PHENOLS TO P-BENZOQUINONES

The present invention relates to a process for preparing alkyl substituted p-benzoquinones by reacting alkyl substituted phenols with molecular oxygen in the presence of metal phthalocyanine catalysts and solvents.

Benzoquinones represent important intermediate materials in the manufacture of hydroquinones which are used as various antioxidants and chemical intermediates. Benzoquinones have heretofore been obtained from the corresponding phenols by treatment with oxidizing agents, such as sodium dichromate and peracetic acid in acid media. However, these methods use a stoichiometric amount of the oxidizing agent with only moderate yields and are uneconomical.

The prior art also describes the use of phthalocyanine related catalysts for the oxidation of alkyl substituted phenols. Without exception the prior art recognizes the difficulty of direct oxidation of phenols to p-benzoquinone realizing instead only mixed products containing very little benzoquinone and mostly biphenoquinones.

It is an object of the present invention to provide a process for the preparation of bialkylated benzoquinones from bialkyl phenols. It is a further object of the invention to provide an improved method for oxidizing an alkyl phenol to obtain alkylated-p-benzoquinones. Other objects will become apparent as the description proceeds.

The above objects are accomplished by reacting alkylated phenols with oxygen in the presence of a catalytic amount of metal phthalocyanine having the following structural formula.

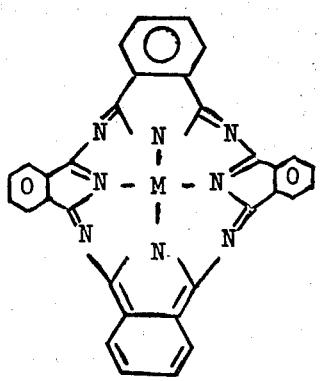

wherein M is selected from the group consisting of Cupric copper hereinafter designated Cu(II) and cobaltous cobalt hereinafter designated Co(II) in a solvent selected from the group consisting of (I) n-alkyl substituted amides, (II) sulfoxides, and (III) alkanols. The n-alkyl substituted amides have the following structural formula

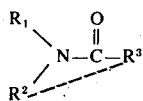

wherein $R^1$, $R^2$ and $R^3$ are selected from the group consisting of hydrogen, alkyl radicals having one to 10 carbon atoms, cycloalkyl radicals having five to 10 carbon atoms, aryl radicals having six to 12 carbon atoms and aralkyl radicals having seven to 15 carbon atoms and wherein $R^2$ and $R^3$ can form a closed chain or heterocyclic ring containing five to 10 carbon atoms, and the sulfoxides (II) have the following structural formula

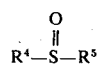

wherein $R^4$ and $R^5$ are the same or different radicals selected from the group consisting of alkyl radicals having from one to 10 carbon atoms, cycloalkyl radicals having five to 10 carbon atoms, aryl radicals having six to 12 carbon atoms and aralkyl radicals having seven to 15 carbon atoms and the alkanols (III) contain from one to four carbon atoms.

Representative examples of radicals of the above formula are alkyl radicals such as methyl, ethyl, propyl, butyl, hexyl, octyl and decyl. Cycloalkyl radicals include cyclopentyl, cyclohexyl and cycloheptyl; aryl radicals such as phenyl and naphthyl; and aralkyl radicals such as methylphenyl and butylphenyl.

Representative examples of solvents useful in this invention are illustrated in the groups below.

| Group I Amides |
| --- |
| Dimethylformamide (DMF) |
| Cyclohexylmethylformamide |
| Diphenylformamide |
| Phenylmethylformamide |
| 1-Methyl-2-pyrrolidinone |

| Group II Sulfoxides |
| --- |
| Dimethylsulfoxide (DMSO) |
| Cyclohexylmethylsulfoxide |
| Phenylmethylsulfoxide |

| Group III Alcohols |
| --- |
| Methanol |
| Ethanol |

Representative examples of catalysts of this invention include cobalt (II) phthalocyanine and copper (II) phthalocyanine.

Of the above dimethylformamide has a high ignition point and high flash point.

Throughout this specification and claims the term "monoalkylphenol" refers to both 2-monoalkylphenols and 3-monoalkylphenols. The term "dialkylphenol" refers to 2,6-di-alkylphenol, 2,5-di-alkylphenol and 2,3-di-alkylphenol. No reaction to the p-benzoquinone form occurred when the phenol was substituted in the 4 position.

The process of this invention can be carried out at a temperature in the range of from about 0° C. to about 100° C., usually at a temperature in the range of from about 15° C. to about 50° C. under a pressure of oxygen bearing gas of from 10 pounds per square inch (psi) to 1,000 pounds per square inch, generally at pressures from 10 to 100 pounds per square inch pressure in the presence of a catalyst. The amount of catalyst used is from one-half mole percent to 15 mole percent catalyst per mole of phenol, preferably from one mole percent to 10 mole percent catalyst per mole of phenol. The concentration of phenol being oxidized in the solution will generally be from 5 to 60 percent by weight based on the weight of the solvent used, usually in the range of from about 5 percent to about 30 percent.

The process of the invention is illustrated in the following examples, parts and percentages being by weight unless otherwise specified.

Phenols were oxidized with cobalt (II) phthalocyanine in several different solvents. The results are shown in Table I below.

Table I

| Cobalt(II) Phthalocyanine Reactions | | | | | |
|---|---|---|---|---|---|
| Mole % Catalyst | Solvent | Phenol | Temp. °C. | Time (hrs) | *BQ Yield % |
| 4 | DMF | 2,6-di-t-butylphenol | 22–27 | 3 | 73 |
| 4–5 | DMSO | 2,6-di-t-butylphenol | 22–29 | 19 | 5.5 |
| 7 | Methanol | 2,6-di-t-butylphenol | 22–32 | 6 | 8.4 |
| 5 | DMF | 2,6-dimethylphenol | 21–28 | 5 | 100 |
| 4 (reused) | DMF | 2,6-di-t-butylphenol | 22–26 | 17 | 12.0 |

*Indicates conversion to corresponding p-benzoquinone.

EXAMPLE 1

1.0 Gram cobalt phthalocyanine was suspended in 10 cubic centimeters (cc) of dimethylformamide (DMF). The suspension was placed in a 500 cubic centimeter Parr bottle. To this catalyst suspension was then added 8.0 grams of 2,6-di-t-butylphenol dissolved in 50 cubic centimeters of DMF along with another 15 cubic centimeters DMF used to wash any residue from the flask which contained the solution. The bottle was clamped in a Parr equipment. The gas in the system was evacuated and the equipment pressurized with 65 pounds per square inch pressure oxygen gas at a temperature of 25° C. The bottle was rocked (agitated) continuously. A pressure drop was noted as the reaction occurred, and the temperature rose about 5° C. After three hours reaction time, no further pressure drop was apparent. The equipment was adjusted to atmospheric pressure and the bottle was removed from the Parr equipment. The reaction mixture was filtered to remove most of the cobalt phthalocyanine catalyst and 3,3′,5,5′-tetratertiarybutyldiphenoquinone.

The 3,3′,5,5′-tetratertiarydiphenoquinone was separated from the cobalt phthalocyanine by extracting it in diethyl ether. The ether was evaporated and 2.10 grams of pure 3,3′,5,5′-tetratertiarybutyldiphenoquinone was obtained (26 percent yield). After removal of the catalyst and the 3,3′,5,5′-tetratertiarydiphenoquinone, the filtrate was analyzed to determine the phenol conversion. The selectivity to 2,6-di-t-butyl-p-benzoquinone was 5.85 grams or 73 percent. Benzoquinone was isolated by removing the DMF on a rotary evaporator and extracting the solid in methanol and evaporating the methanol extract. The residue was dissolved in acetic acid and the 2,6-di-t-butyl-p-benzoquinone was crystallized on addition of water to the hot acetic acid solution.

EXAMPLE 2

2,6-Dimethylphenol was oxidized in the same manner as described in Example 1, using 1.0 gram of cobalt phthalocyanine and 5.0 grams of 2,6-dimethylphenol in 75 cubic centimeters of DMF. The solution was reacted under 67 pounds per square inch oxygen pressure and at a temperature between 21° C. and 28° C. After three hours 96 percent of the 2,6-dimethylphenol was oxidized to the corresponding p-benzoquinone. After 5 hours reaction time, 100 percent conversion was obtained. The benzoquinone was isolated in 95 percent of the theoretical amount by evaporating the reaction mixture to dryness and extracting it with petroleum ether. The product had a melting point between 70° C. and 72° C.

It can be seen that cobalt (II) phthalocyanine is a very effective catalyst for the oxidation of alkylated phenols in dimethylformamide. Higher temperatures tend to yield progressively more of the diphenoquinone instead of the desired p-benzoquinone.

The examples above illustrate the invention using cobalt (II) phthalocyanine as a catalyst. Copper (II) phthalocyanine is also an effective catalyst in the process of the invention.

Monoalkyl phenols and phenol itself have very low conversion rates and yield only trace amounts of benzoquinone.

Representative examples of dialkylphenols that can be oxidized in the process of this invention are 2,6-di-t-butylphenol; 2,6-dimethylphenol; 2,6-dihexylphenol; 2,6-dipropylphenol; 2,6-dioctylphenol and 2-methyl-6-butylphenol.

Representative examples of p-benzoquinones that can be prepared by the process disclosed in this invention are 2,6-di-t-butyl-p-benzoquinone; 2,6-dimethyl-p-benzoquinone; 2,6-dihexyl-p-benzoquinone; 2,6-dipropyl-p-benzoquinone; 2,6-dioctyl-p-benzoquinone and 2-methyl-6-t-butyl-p-benzoquinone.

While certain representative embodiments and details have been shown for the purpose of illustrating this invention, it will be apparent to those skilled in this art that various changes and modifications can be made herein without departing from the spirit or scope of this invention.

I claim:

1. A process which comprises reacting an alkylated phenol selected from the group consisting of 2,6-dialkylphenol, 2,5-dialkylphenol and 2,3-dialkylphenol wherein the alkyl groups contain from one to eight carbon atoms with oxygen or oxygen bearing gas at a temperature of from about 0° C. to about 100° C. at a pressure of from about 10 pounds per square inch to about 1,000 pounds per square inch in the presence of from about ½ mole percent to 15 mole percent per mole of alkylated phenol of a cobalt phthalocyanine catalyst of the general formula

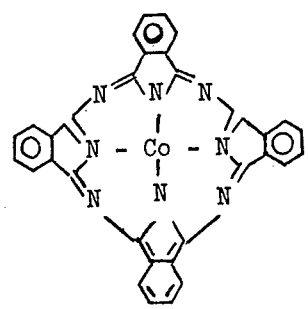

in the presence of a solvent selected from the group consisting of (I) n-alkyl substituted amides selected from the group consisting of dimethylformamide, cyclohexylmethylformamide, diphenylformamide, phenylmethylformamide, and 1-methyl-2-pyrrolidinone, (II) sulfoxides selected from the group consisting of dimethylsulfoxide, cyclohexylmethylsulfoxide, and phenylmethylsulfoxide, and (III) alkanols selected from the group consisting of methanol and ethanol.

2. A process as described in claim 1 wherein the metal catalyst is cobalt (II) phthalocyanine and the phenol is a bialkylated phenol selected from the group consisting of 2,6-di-t-butylphenol; 2,6-dimethylphenol; 2,6-dihexylphenol; 2,6-dipropylphenol; 2,6-dioctylphenol and 2-methyl-6-t-butylphenol, and wherein the reaction is carried out at a pressure of from 10 pounds per square inch to 100 pounds per square inch pressure of oxygen bearing gas and the temperature is from 15° C. to 50° C. and the catalyst concentration is in the range of from 1 mole percent catalyst to 10 mole percent catalyst per mole of phenol.

3. A process as described in claim 1 wherein the phenol is selected from the group consisting of 2,6-di-t-butylphenol and 2,6-dimethylphenol, the reaction is carried out in dimethylformamide at a pressure of from 10 to 100 pounds per square inch pressure of oxygen-bearing gas, the temperature is from 15° C. to 50° C. and a cobalt phthalocyanine catalyst is used in a concentration of from 1 mole percent catalyst per mole of phenol to 10 mole percent catalyst per mole of phenol.

4. A process as described in claim 1 wherein a solution of from 5 to 30 percent by weight of 2,6-di-t-butylphenol in dimethylformamide is reacted with oxygen in the presence of cobalt (II) phthalocyanine at a pressure of from 10 to 100 pounds per square inch pressure oxygen bearing gas at a temperature of from 15° C. to 50° C.

5. A process which comprises reacting an alkylated phenol selected from the group consisting of 2,6-dialkylphenol, 2,5-dialkylphenol and 2,3-dialkylphenol wherein the alkyl groups contain from one to eight carbon atoms with oxygen or oxygen bearing gas at a temperature of from about 0° C. to about 100° C. at a pressure of from about 10 pounds per square inch to about 1,000 pounds per square inch in the presence of from about ½ mole percent to 15 mole percent per mole of alkylated phenol of a copper phthalocyanine catalyst of the general formula

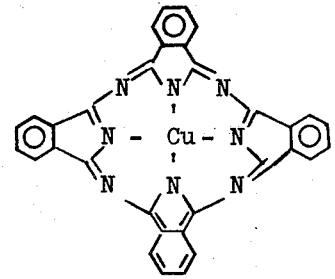

in the presence of a solvent selected from the group consisting of (I) n-alkyl substituted amides selected from the group consisting of dimethylformamide, cyclohexylmethylformamide, diphenylformamide, phenylmethylformamide, and 1-methyl-2-pyrrolidinone, and (II) sulfoxides selected from the group consisting of dimethylsulfoxide, cyclohexylmethylsulfoxide, and phenylmethylsulfoxide.

* * * * *